(12) United States Patent
Samadani et al.

(10) Patent No.: US 12,339,873 B2
(45) Date of Patent: Jun. 24, 2025

(54) INCREMENTAL CLUSTERING AND HIERARCHY FORMATION SYSTEM FOR CLINICAL DECISION SUPPORT (CDS) SYSTEM DEVELOPMENT AND METHOD OF OPERATION THEREOF

(71) Applicant: KONINKLIJKE PHILIPS N.V., Eindhoven (NL)

(72) Inventors: Ali Akbar Ahmad Samadani, Cambridge, MA (US); Taiyao Wang, Cambridge, MA (US); Cornelis van Zon, Cambridge, MA (US)

(73) Assignee: Koninklijke Philips N.V., Eindhoven (NL)

( * ) Notice: Subject to any disclaimer, the term of this patent is extended or adjusted under 35 U.S.C. 154(b) by 373 days.

(21) Appl. No.: 17/978,482

(22) Filed: Nov. 1, 2022

(65) Prior Publication Data

US 2023/0197287 A1    Jun. 22, 2023

Related U.S. Application Data

(60) Provisional application No. 63/291,528, filed on Dec. 20, 2021.

(51) Int. Cl.
*G06F 17/00* (2019.01)
*G06F 16/28* (2019.01)
(Continued)

(52) U.S. Cl.
CPC ............ *G06F 16/285* (2019.01); *G06F 18/23* (2023.01); *G06F 18/24147* (2023.01); *G16H 10/60* (2018.01); *G16H 50/70* (2018.01)

(58) Field of Classification Search
CPC .. G06F 16/285; G06F 18/23; G06F 18/24147; G16H 10/60; G16H 50/70; G16H 50/30; G16H 40/20
See application file for complete search history.

(56) References Cited

U.S. PATENT DOCUMENTS 9,268,915 B2 * 2/2016 Holmes ................. G16H 50/20
10,770,184 B1 * 9/2020 McNair ................. G16H 50/70
(Continued)

FOREIGN PATENT DOCUMENTS

CN    113035338 A    6/2021
WO    2021139146 A1   7/2021

OTHER PUBLICATIONS

Carmela Comito et al., A clinical decision support framework for automatic disease diagnoses. In Proceedings of the 2019 IEEE/ACM International Conference on Advances in Social Networks Analysis and Mining. Association for Computing Machinery, 933-936, < https://doi.org/10.1145/3341161.3343509> Aug. 2019.*

(Continued)

*Primary Examiner* — Greta L Robinson
(74) *Attorney, Agent, or Firm* — Daniel H. Brean

(57) ABSTRACT

A CDS system including a controller extracting EHRs of an IHG and selecting SMs to form a target patient database, capturing a time interval between each subsequent record for each of the measurements defined by the SMs, computing hospital level features including statistics on the distribution of the captured time intervals for each of the measurements, clustering the plurality of hospitals of the IHG in accordance with the computed hospital level features, determining whether an other hospital is within a threshold distance to a closest one of the plurality of clusters; placing the other hospital in the closest cluster when it is determined that the other hospital is within the threshold distance, and placing the other hospital in a new cluster when it is determined that the other hospital is not within the threshold distance.

20 Claims, 8 Drawing Sheets

(51) Int. Cl.
  *G06F 18/23*     (2023.01)
  *G06F 18/2413*   (2023.01)
  *G16H 10/60*     (2018.01)
  *G16H 50/70*     (2018.01)

(56)          References Cited

U.S. PATENT DOCUMENTS

2014/0358926 A1* 12/2014 McGregor .......... G06F 16/2477
                                                  707/736
2015/0339442 A1   11/2015 Oleynik
2018/0174687 A1    6/2018 Ayvazian

OTHER PUBLICATIONS

Pollard, T.J. et al. "The eICU Collaborative Research Database, a freely available multi-center database for critical care research." Sci Data 5, 180178 (2018).

* cited by examiner

500

SELECT TARGET PATIENT GROUP: — 501
☒ Mechanically Ventilated Patients (MVPs)
☐ Ventilation associated pneumonia (VAP)

PHYSIOLOGICAL MEASURMENTS — 503
IMAGING:
☒ X-RAY — 505
☐ CT SCAN
☐ ULTRASOUND

CARDIO-PULMINARY — 507
☒ BLOOD PRESSURE
☒ PULSE RATE
☒ $SpO_2$
☒ $CO_2$

OTHER

SELECT New Hospital: — 509
☒ Hospital-21
☐ Hospital-22

FEATURE DETERMINATION — 511
☐ Manual Entry
☒ Automatic feature determination

FIG. 5

INCREMENTAL CLUSTERING AND HIERARCHY FORMATION SYSTEM FOR CLINICAL DECISION SUPPORT (CDS) SYSTEM DEVELOPMENT AND METHOD OF OPERATION THEREOF

CROSS-REFERENCE TO RELATED APPLICATIONS

This patent application claims the priority benefit under 35 U.S.C. § 119(e) of U.S. Provisional Application No. 63/291,528, filed on Dec. 20, 2021, the contents of which are herein incorporated by reference.

FIELD OF THE PRESENT SYSTEM

The present system relates to a clustering and hierarchy formation system for hospitals to guide their clinical decision support (CDS) system and more particularly, to data-driven clustering and hierarchy formation system for hospitals to enhance artificial intelligence (AI) based clinical decision support (CDS) system and a method of operation thereof.

BACKGROUND OF THE PRESENT SYSTEM

Conventional clinical decision support (CDS) systems are oblivious to inter-hospital differences in terms of what data is available and at what frequency the data is acquired at different hospitals. Such differences result in missing, infrequent, or different types of measurements for the same patient at different hospitals. These inter-hospital differences pose a serious challenge to the success of the CDS tools when deployed in a hospital that is different from the ones used to build the CDS tool.

Hospitals may vary along many dimensions including size, facilities, and specialization. Furthermore, different clinical protocols may be used to manage the same patient at different hospitals. For instance, for a mechanically ventilated patient (MVP), different types of measurements and interventions may be performed at different frequencies in two different hospitals. As a result, if the same patient was admitted at different times to these different hospitals, inter-hospital differences in their care practices might lead to different types and levels of data being available for this patient when treated at these two different hospitals. These inter-hospital differences can have an adverse effect on the outcome of treatment for the patient.

The present inventors have found that the success of data driven CDS tools relies heavily upon the availability of the right data at the time of decision making (e.g., CDS decision making). For example, when a CDS tool is built without regard to inter-hospital differences in data availability, the CDS tool is likely going to fail and be deemed unreliable due to differences in data availability between design and target hospitals. For example, if a CDS tool relies on the physiological measurement of end-tidal carbon dioxide ($etCO_2$), where for a test patient $etCO_2$ is never measured, then the CDS tool cannot make an informed decision. To overcome the aforementioned barriers and detriments as well as others, there is a need for a CDS system that may characterize inter-hospital differences prior to the development of a CDS system to help: 1) assess if and how a CDS tool can be deployed in a specific hospital, and 2) identify clusters of similar hospitals and build one or more separate CDS tools that may be tailored to each cluster. Thus, there is a need to overcome the aforementioned barriers, by determining novel ways to effectively provide CDS tools which can account for one or more of intra-hospital and inter-hospital differences and thereby output CDS services with increased accuracy and performance.

SUMMARY OF THE PRESENT SYSTEM

The system(s), device(s), method(s), arrangements(s), interface(s), computer program(s), processes, etc., (hereinafter each of which will be referred to as system, unless the context indicates otherwise), described herein address problems in prior art systems.

In accordance with embodiments of the present system, there is disclosed a clinical decision support (CDS) system, including at least one controller configured to: extract electronic health records (EHRs) of a plurality of hospitals of an initial hospital group (IHG) in accordance with at least one of a selected target patient population (TPP) and selected physiological measurements of interest (SMs) to form a target patient database; compute patient level features of the target patient dataset capturing a time interval between each subsequent record for each of the measurements defined by the SMs; compute hospital level features of the target patient dataset comprising statistics descriptive of the distribution of the captured time intervals for each of the measurements defined by the SM in the computed patient level features; cluster the plurality of hospitals of the IHG in accordance with the computed hospital level features into a plurality of clusters (CL); determine whether an other hospital (148, 301-NH) is within a threshold distance (d) to a closest one of the plurality of clusters; place the other hospital in the closest cluster when it is determined that the other hospital is within the threshold distance to the closest one of the plurality of clusters; and place the other hospital in a new cluster of the plurality of clusters when it is determined that the other hospital is not within the threshold distance to the closest one of the plurality of clusters.

The present system may include at least one controller configured to create at least one CDS tool tailored to each cluster of the plurality of clusters and associate the CDS tool with the corresponding cluster of the plurality of clusters. The at least one controller may be configured to render information related to the at least one CDS tool in association with the corresponding cluster of the plurality of clusters. The at least one controller may be configured to render information related to required physiological settings corresponding to a selected model associated with a cluster.

The at least one controller may be configured to compare an EMR profile for the other hospital with that of an EMR profile of at least one of the hospitals of the IHG. The at least one controller may be configured to determine physiological measurements available to the other hospital. The at least one controller may be configured to compare the physiological measurements available to the other hospital with physiological measurements required by a model and render results of the comparison. The at least one controller may be configured to render a plurality of models in association with each cluster on a display of the system for selection by a user.

In accordance with embodiments of the present system, there is disclosed a clinical decision support (CDS) system, including: at least one controller configured to: receive selections corresponding to selected physiological measurements of interest (SMs) and a selected target patient population (TPP); extract electronic health records (EHRs) (114) of a plurality of hospitals (101-x) of an initial hospital group (IHG) in accordance with at least one of a selected TPP and SMs to form a target patient dataset; compute patient level features capturing a time interval between each subsequent record for each measurement defined by the SMs; compute hospital level features comprising statistics descriptive of the distribution of the captured time intervals for each of the measurements defined by the SM in the computed patient level features; cluster the plurality of hospitals of the IHG in accordance with the computed hospital level features into a plurality of clusters (CL); determine whether an other hospital is within a threshold distance (d) to a closest one of the plurality of clusters; place the other hospital in the closest cluster when it is determined that the other hospital is within the threshold distance to the closest one of the plurality of clusters; and place the other hospital in a new cluster of the plurality of clusters when it is determined that the other hospital is not within the threshold distance to the closest one of the plurality of clusters.

The at least one controller may be configured to create at least one CDS tool tailored to each cluster of the plurality of clusters and associating the CDS tool with the corresponding cluster of the plurality of clusters. The at least one controller may be configured to render information related to the at least one CDS tool in association with the corresponding cluster of the plurality of clusters. The at least one controller may be configured to render information related to required physiological settings corresponding to a selected model associated with a cluster. The at least one controller may be configured to compare an EHR profile for the other hospital with that of an EMR profile of at least one of the hospitals of the IHG. The at least one controller may be configured to determine physiological measurements available to the other hospital.

The at least one controller may be configured to compare the physiological measurements available to the other hospital with physiological measurements required by a model and render results of the comparison. The at least one controller may be configured to render a plurality of models in association with each cluster on a display of the system for selection by a user. The system may include a display (146) coupled to the controller, wherein the at least one controller may be configured to control the display to render a graphical user interface (GUI) including selection items for the user to select the selections corresponding to selected physiological measurements of interest (SMs) and a selected target patient population (TPP) from a user.

In accordance with embodiments of the present system, there is disclosed a clinical decision support (CDS) system, including: at least one controller configured to: compute patient level features capturing a time interval between each subsequent record for each measurement defined by selected physiological measurements of interest (SMs) from electronic health records of a target patient population (TPP) of a plurality of hospitals of an initial hospital group (IHG); compute hospital level features comprising statistics descriptive of the distribution of the captured time intervals for each of the measurements defined by the SM in the computed patient level features; cluster the plurality of hospitals of the IHG in accordance with the computed hospital level features into a plurality of clusters (CL); determine whether an other hospital is within a threshold distance (d) to a closest one of the plurality of clusters; place the other hospital in the closest cluster when it is determined that the other hospital is within the threshold distance to the closest one of the plurality of clusters; and place the other hospital in a new cluster of the plurality of clusters when it is determined that the other hospital is not within the threshold distance to the closest one of the plurality of clusters.

The at least one controller may be configured to create least one CDS tool tailored to each cluster of the plurality of clusters and associate the CDS tool with the corresponding cluster of the plurality of clusters. The at least one controller may be configured to render information related to the at least one CDS tool in association with the corresponding cluster of the plurality of clusters.

BRIEF DESCRIPTION OF THE DRAWINGS

It should be expressly understood that the drawings are included for illustrative purposes and do not represent the scope of the present system. It is to be understood that the figures may not be drawn to scale. Further, the relation between objects in a figure may not be to scale and may in fact have a reverse relationship as to size. The figures are intended to bring understanding and clarity to the structure of each object shown, and thus, some features may be exaggerated in order to illustrate a specific feature of a structure. In the accompanying drawings, like reference numbers in different drawings may designate identical or similar elements, portions of similar elements and/or elements with similar functionality. The present system is explained in further detail, and by way of example, with reference to the accompanying drawings which show features of various exemplary embodiments that may be combinable and/or severable wherein:

FIG. 5 shows a graphical user interface generated and rendered by the system in accordance with embodiments of the present system.

DETAILED DESCRIPTION OF THE PRESENT SYSTEM

Figure 1:
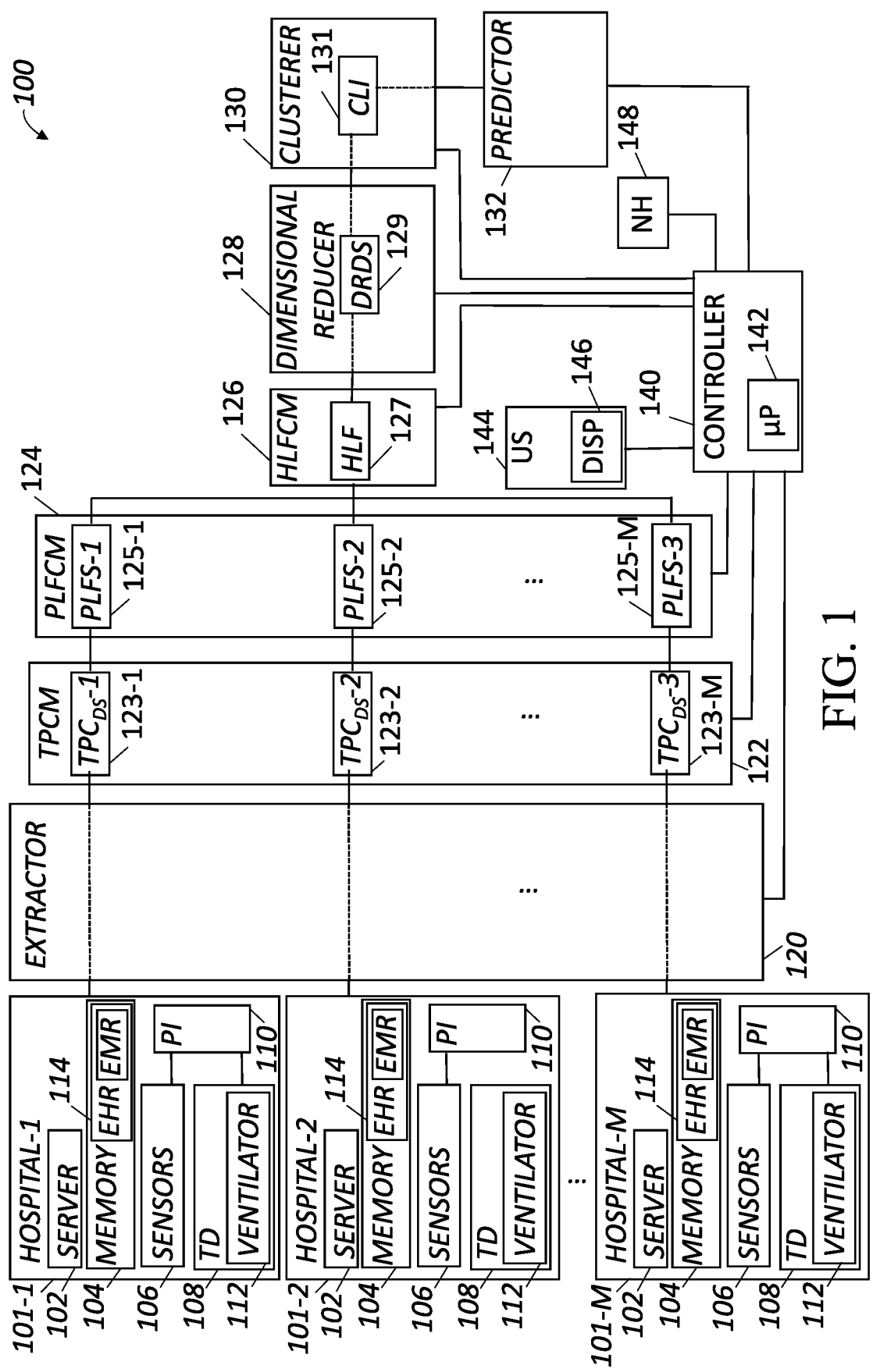
FIG. 1 is an illustration of a schematic block diagram of a CDS system operating in accordance with embodiments of the present system.

The following are descriptions of illustrative embodiments that when taken in conjunction with the following drawings will demonstrate the above noted features and advantages, as well as further ones. In the following description, for purposes of explanation rather than limitation, illustrative details are set forth such as architecture, interfaces, techniques, element attributes, etc. However, it will be apparent to those of ordinary skill in the art that other embodiments that depart from these details would still be understood to be within the scope of the appended claims. Moreover, for the purpose of clarity, detailed descriptions of well-known devices, circuits, tools, techniques, and methods are omitted so as not to obscure the description of the present system.

The term "and/or," and formatives thereof, should be understood to mean that only one or more of: the recited elements may need to be suitably present (e.g., only one recited element is present, two of the recited elements may be present, etc., up to all of the recited elements may be present) in a system in accordance with the claims recitation and in accordance with one or more embodiments of the present system. In the context of the present embodiments, the terms "about", "substantially" and "approximately" denote an interval of accuracy that a person skilled in the art will understand to still ensure the technical effect of the feature in question which in some cases may also denote "within engineering tolerances". The term may indicate a deviation from the indicated numerical value of ±20%, ±15%, ±10%, ±5%, ±1% ±0.5% or ±0.1%.

As used herein, the terms hospital, hospitals, or formatives thereof, may include hospitals, health centers, health clinics, health facilities, nursing facilities, rehabilitation facilities, urgent care facilities, medical provider, enterprise health provider, and/or the like, each of which may be commonly referred to as hospital or hospitals, for the sake of clarity unless the context indicates otherwise. Thus, for the sake of clarity, in the following embodiments reference will be made to hospitals unless the context indicates otherwise. The terms user, users, or formatives thereof may refer to a user, operator, clinician, technician, and/or the like unless the context indicates otherwise. The terms patient, patients, or formatives thereof, may include patients or other individuals (e.g., subjects, etc.) for which a hospital or other medical provider, has generated an electronic medical record (EMR) and stored it in the patient's electronic health record (EHR). As readily appreciated, electronic medical records (EMRs) are the digital form of the paper charts that were used in the past. An electronic medical record contains the past medical history, medications, visit summaries, demographic and insurance information, etc., however, might have a format that is hard to share across practices, hospitals, etc. In contrast, electronic health records (EHRs) provide a more holistic view of the patient journey including their encounters with different healthcare providers over time. EHRs are designed to be accessible by all professionals involved in a patient's care, from the physicians, to nurses, to laboratories and even the patients themselves. With advancements in wearable health tracking technologies, future EHRs will provide integration with consumer-level wearable devices enabling continuous health monitoring.

It should be appreciated that embodiments of the present system may provide a CDS system which may provide enhanced CDS decision making for patients undergoing one or more complications such as ventilation-associated pneumonia (VAP) and/or the like. Accordingly, the embodiments herein may discuss a CDS system for VAP management (e.g., risk estimation and treatment) for the sake of clarity although are understood to be applicable to any patient care. However, it should be understood that embodiments of the present system may also provide a CDS system for other types of therapy, such as radiology therapy, stroke therapy, etc. It is further appreciated that a CDS system in accordance with the present embodiments may be deployed for any type of diagnostic and therapeutic medical care that may be required.

As used herein the term electronic health record (EHR) may refer to EHRs which may include one or more of electronic medical records (EMRs) and personal health records (PCRs). For the sake of clarity, it will be assumed that for each hospital, its EHRs may include a plurality of EMRs that are created during interactions (e.g., physiological interactions) with a corresponding patient. Thus, a patient of a hospital may have an EHR which may include a plurality of EMRs.

FIG. 1 is an illustration of a schematic block diagram of a CDS system 100 (hereinafter the system 100) operating in accordance with embodiments of the present system. The system 100 may include one or more of: one or more hospitals 101-1 through 101-M (generally 101-x, where M is an integer), an extractor 120, a target patient cohort memory (TPCM) 122, a patient-level feature computation module (PLFCM) 124, a hospital-level feature computation module (HLFM) 126, a dimensional reducer 128, a clusterer (CL) 130, a predictor 132, a controller 140, a new hospital (NH) 148, and a user station (US) 144, one or more of which may be local or remotely located relative to each other and may communicate with each other directly and/or via a network using any suitable communication method or methods or such as wired, optical, and/or wireless communication methods. One or more of the extractor 120, the PLFCM 124, HLFM 126, the dimensional reducer 128, the CL 130, the predictor 132, and the controller 140 may include a neural network processor or the like and two or more may be combined together or separated further. In addition, one or more of the extractor 120, the PLFCM 124, HLFM 126, the dimensional reducer 128, the CL 130, and the predictor 132 may form a portion of the controller 140 (e.g., an executed programming portion).

The controller 140 may control the overall operation of the system 100 and may include one or more logic devices such as at least one micro-processor 142 (µP) or the like. It is envisioned that the controller 140 may be singular or may include a plurality of controllers distributed throughout the system 100, one or more of which may communicate with one or more other controllers using any suitable method or methods.

The US 144 may include any suitable device or devices with which a user may interact with the system such as a terminal, a therapeutic device, a personal computer (PC), a laptop, a tablet, a smart phone, and/or the like, and may include a rendering device such a display 146, a speaker, a haptic device, etc., which the system may render information received, stored, and/or generated by the system 100 such as CDS information, EMRs, EHRs, system setting information (SSI), system alerts, etc., under the control of the controller 140. The US 144 may further include at least one user input device such as a keyboard, a microphone, a mouse, a stylus, a trackball, a touchscreen, etc., with which a user may interact to enter information to be used by the system 100 such as system settings, parameters, (e.g., to be stored in the system setting information (SSI), and/or information to be stored in EHRs, EMRs, etc.). The US 144 may communicate with the controller 140 using any suitable communication method or methods such as wired, optical, wireless, etc. For example, it is envisioned that the US 144 may include a wireless device such as a tablet, a smartphone, etc., which may communicate with other portions of the system 100 using any suitable wireless communication method or methods via any suitable network such as WiFi™, Bluetooth™, a cellular network, an ad-hoc network, the Internet, etc. Similarly, the controller 140 may communicate with the hospitals 101-x via any suitable communication network.

With regard to the one or more hospitals 101-x, for the sake of clarity, it will be assumed that these hospitals 101-x may each include one or more of a server 102, a memory 104, sensors 106, a therapeutic device (TD) 108, and a patient interface (PI) 110, one or more of which operate under the control of a controller and may communicate with each other via any suitable method such as via wired and/or wireless networks.

The server 102 may control the overall operation of the corresponding one or more hospitals 101-x and may include one or more controllers which may control the overall operation of the corresponding server 102. The controller 140 may communicate with the server 102 via a wired and/or wireless network. The server 102 may obtain information related to physiological measurements (PMs) captured by the one or more sensors 106 and store this information as an EMR in an EHR 114 in the memory 104.

The memory 104 may include one or more memories which may be local and/or distributed (e.g., a cloud memory, etc.) and may store information such as, for example, the SSI and/or the EHR 114. The EHR 114 may include a plurality of EHRs each of which may include information such as EMRs of one or more patients of the corresponding hospital 101-x and its affiliated clinics and may include information which may reflect the actual practice and documentation of care at each respective hospital. Accordingly, the memory 104 of a corresponding hospital may store the hospital's EHRs 114 which may include EMRs for each respective patient. Thus, the system may further store features of each corresponding respective hospital in its corresponding EMR such as high-level hospital characteristics (HLHCs) such as number of beds, intensive unit (ICU) types available (e.g., cardiac, ambulatory, etc.), etc. In some embodiments, HLHCs may be derived through an analysis of the EMRs to determine the HLHCs or may be entered directly by a user. Information in the memory 104 may be employed by the system to determine and form hospital clusters as may be discussed below with reference to FIGS. 2 through 3F below.

The PI 110 may provide an interface between the TD 108 and the patient receiving therapy from the TD 108 and/or being observed (such as for vitals, gasses, etc.). The PI 110 may include one or more PIs which may be local or distributed relative to each other. There may be one or more PIs 110 associated with a patient. For example, the PIs 110 may include a pulse oximeter and a blood pressure sensor which may provide corresponding information which may then be recorded in the EMR of the patient. In yet other embodiments, the PIs 110 may include one or more signal acquisition transducers for image acquisition. In yet other embodiments, the PIs 110 may include a face mask coupled to the ventilator 112. Thus, it is seen that then PIs 110 may interface with the patient to provide therapy and/or collect sensory information for use by the server 104. In this regard, the PI 110 may include one or more of the sensors 106.

The TD 108 may include any suitable type of therapeutic device or machine such as a ventilator 112, (e.g., for mechanical ventilation therapy, etc.) which may interface with a patient via the corresponding patient interface (PI) 110. It is also envisioned that the TD 108 may include other types of devices such as an imager (e.g., a magnetic resonance imaging (MRI) scanner, an X-ray scanner, an ultrasound scanner, a computed-tomography (CT) scanner, etc.). The sensors 106 may be located in any suitable location and may, for example, be coupled to the PI 110 and sense corresponding information (e.g., one or more of flow rate, temperature, humidity, pressure, oxygen saturation level ($SpO_2$, etc.), carbon dioxide ($CO_2$), end-tidal carbon dioxide ($etCO_2$), blood pressure (BP), pulse rate (PR), image information (e.g., X-ray, CT, ultrasound, etc.), which may form at least part of the physiological measurements (PMs) and may be distinguished by type (e.g., $O_2$, $etCO_2$, BP, PR, image information, etc.), form corresponding sensor information, and provide this information to the server 102 for further processing and storage in the memory 104 such as in the EMR within the EHR 114 for later processing in accordance with embodiments of the present system. With regard to the type of physiological measurements, each type of physiological measurements may be selected by a user and/or the system as may be set forth in the SSI and may be referred to as a selected physiological measurement (SM). Thus, the SMs may have corresponding PMs. For example, assuming that the (types) of PMs are $SpO_2$, $CO_2$, $etCO_2$, BP, PR, and image information, then one or more of these may be selected as SMs. However, it should be understood that there may be SMs that may not have a corresponding PM in a hospital.

The sensors 106 may include any suitable type of sensors as may be employed in a hospital or patient care environment and may form corresponding sensor information (e.g., based upon their type), and provide this sensor information to the server 102 for further processing, rendering, and/or storage in the memory 104. For example, the server 102 may, process the sensor information (e.g., to detect PR in real time), form a corresponding EMR for a patient and store this EMR in the EHR 114. The TD 108 may include one or more TDs which may the same as or different from each other and may be local or distributed relative to each other. It is also envisioned that the TDs 108 may provide service to one or more patients of the corresponding hospital 101-x.

The sensors 106 may be located at one or more locations associated with the corresponding hospital 101-1 such as at an associated TD 108 sense various information depending upon a type of sensor, form corresponding information, and provide this sensor information to the server 102 for further processing in accordance with embodiments of the present system. The server 102 may obtain the sensor information, process it, and form and/or update a corresponding EMR for a corresponding patient and store this EMR in the EHR 114 of the corresponding hospital 101-x. Thus, the EHR 114 may include EMR for one or more patients of the corresponding hospital 101-x.

The NH 148 may include different and/or similar features as the hospitals 101-x or may be an emulated hospital that may be employed for design, construction and/or evaluation of the present system, depending upon system settings.

The extractor 120 may obtain EHRs including their respective EHRs from each of the hospitals 101-x in accordance with one or more settings such as a target patient population (TPP) (e.g., mechanically ventilated patients in the present embodiments), and may thereafter perform an extraction limited by the SM and may form a corresponding target patient cohort data set ($TPC_{DS}$-1 through $TPC_{DS}$-3) 123-1 through 123-M for each corresponding hospital 101-x. The target patient cohort data set ($TPC_{DS}$-1 through $TPC_{DS}$-3) may include extracted information for a patient cohort of interest (e.g., mechanically-ventilated patients (MVPs) in the present embodiments as set forth by the TPP) as will be described below. The target patient cohort data set (TPC$_{DS}$-1 through TPC$_{DS}$-3 (generally TPC$_{DS}$)) may then be stored in a memory of the TPCM 122 and/or may be provided to the PLFCM 124 for further processing.

The PLFCM 124 may obtain the TPC$_{DS}$-1 through TPC$_{DS}$-3 and may, using any suitable feature computation algorithm, compute features at the patient level including capturing a time interval between each subsequent record for each type of measurement defined by the SM and form corresponding patient level features PLFs-1 through PLFs-3 (generally PLFs) that may be forwarded to the HLFM 126 for further processing.

The HLFM 126 may obtain the PLFs (PLF-1 through PLF-M) for each hospital and compute features at the hospital level therefrom which features may include statistics descriptive of the distribution of patient-level intervals (e.g., median, 25% percentile, 75% percentile) for a given measurement (sensor data, e.g., SpO$_2$), test, imaging data acquisition, etc., (e.g., as set forth by the SM) in the corresponding hospital and form a corresponding hospital level feature computation (HLF) data set 127 which may then be forwarded to the dimensional reducer 128.

The dimensional reducer 128 may receive the HLF data set 127 and process it to project each of the hospitals of an initial hospital group (IHG) into a low-dimensional space (LDS) using conventional dimensionality reduction (DR) techniques such as the principal component analysis (PCA) that projects hospitals to a lower-dimensional space spanned by dimensions of maximum variance between hospitals. In another embodiment, a DR approach may be used that preserves the local neighborhood structure of the hospitals such that in the resulting low-dimensional space, the between-hospitals distances within local neighborhoods are preserved. One such DR technique is the locally-linear embedding. Yet in another embodiment, a non-linear DR technique such as the t-distributed stochastic neighbor embedding can be used that project hospitals in a lower-dimensional space that mimics the hospital distribution in the original high-dimensional space. For all these DR techniques, a manual inspection of the low-dimensional embedding of the hospitals might be needed to verify the results. The resulting low-dimensional embedding forms a DR data set (DRDS) which may then be forwarded to the clusterer 130.

The clusterer 130 may receive the DRDS 129 and may process it to cluster the hospitals 101-$x$ using any suitable clustering techniques such as the k-means, hierarchical, or spectral clustering and may form corresponding cluster information (CLI) 131. The clusterer 130 may then forward the CLI for downstream tasks such as downstream event prediction, VAP prediction, etc., to improve their prediction performance by incorporating CLI in the prediction process. The CLI may be rendered on a rendering device of the system, such as the display 146, for the convenience of the user. For example, one or more of the hospitals 101-$x$ may be graphically depicted in clusters as will be described elsewhere in this application with reference to FIGS. 3A through 3F. The clusterer 130 may provide the CLI to the predictor 132.

The predictor 132 may receive the CLI and may process it using one or more predictive algorithms to form one or more predictive models which may be processed by the system to predict the performance of a hospital 101-$x$ such as a new hospital (101-NH). The predictive models may be employed by the system and/or rendered on a rendering device of the system such as on the display 146.

Using CLI, the predictor 132 may constitute a modular multi-expert predictor in which there is a dedicated model for each cluster of hospitals in CLI. For example, to make predictions for patients at 148-NH, one or more of the models may then be used for CDS decision making based on the proximity of 148-NH to the existing clusters. In another embodiment, the cluster membership information from CLI can be used as a feature alongside other patient-level features for downstream prediction tasks.

In the present embodiments, it will be assumed that the user or system may set, reset, and/or modify the SSI at any time in accordance with embodiments of the system. For example, the user may enter settings during operation and the system 100 may update the SSI.

Figure 2:
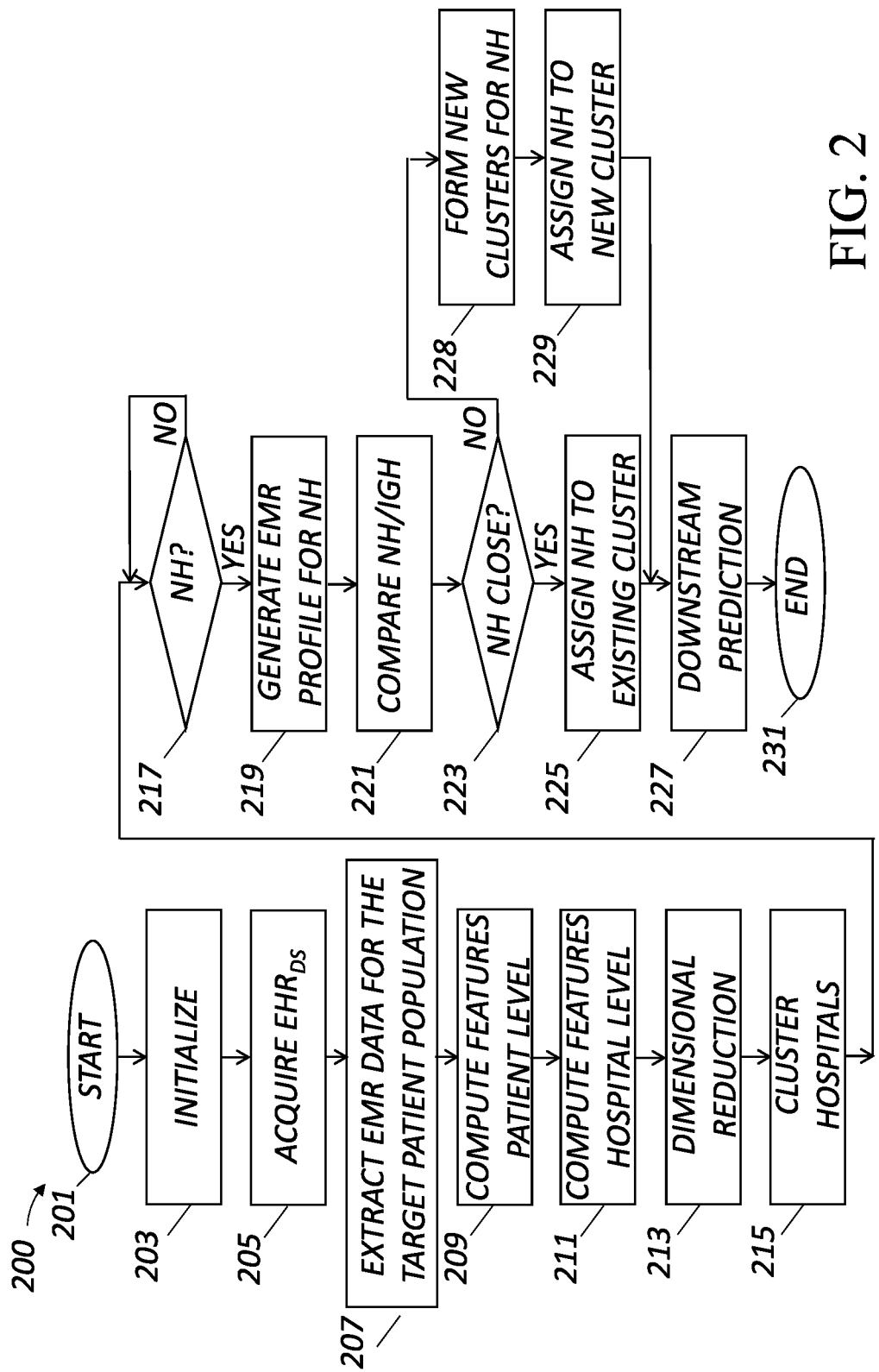
FIG. 2 is an illustration which shows a functional flow diagram performed by a process in accordance with embodiments of the present system.
Figures 3A, 3B:
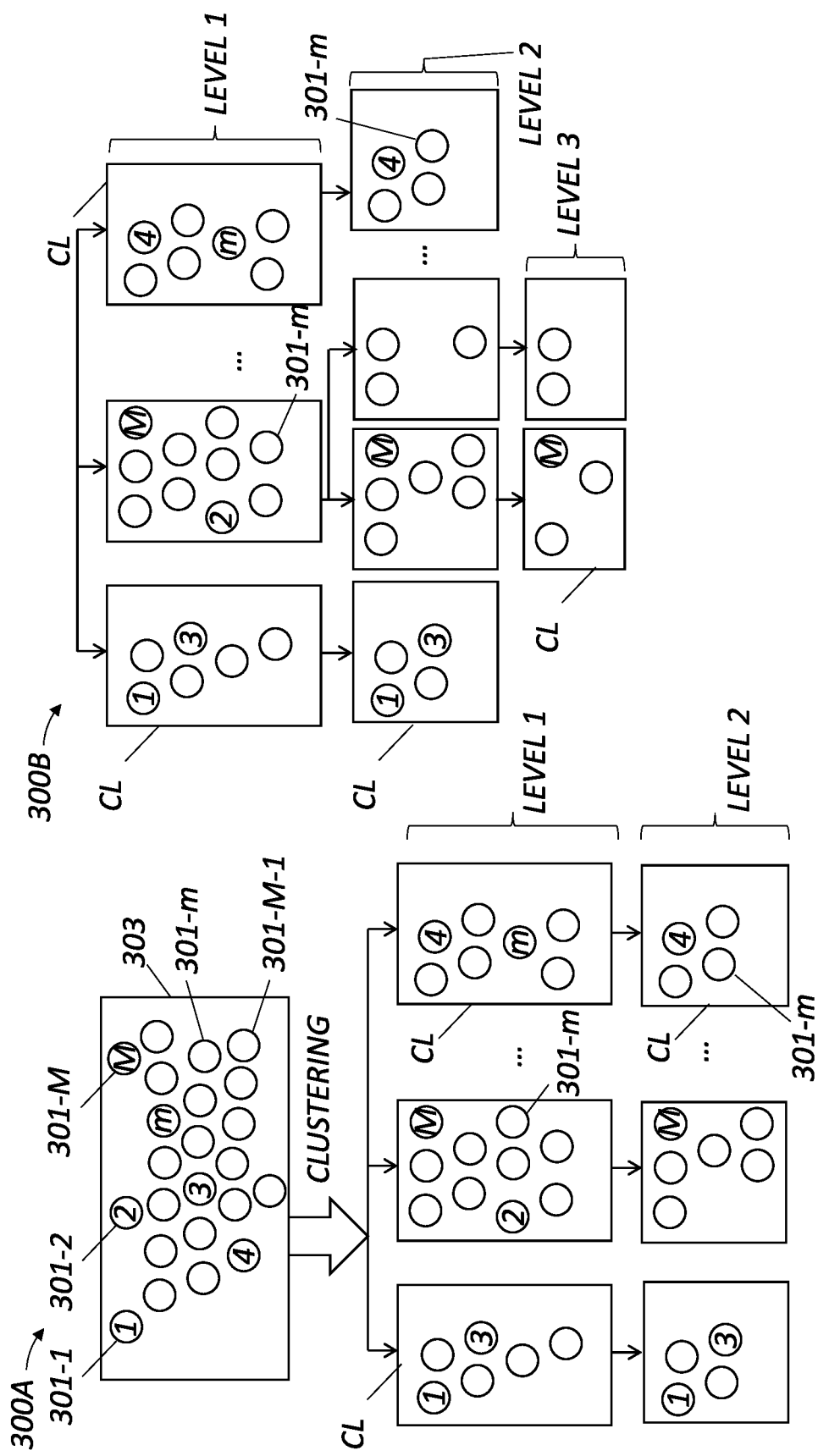
FIG. 3A is an illustration which shows a graph depicting a hospital clustering method performed in accordance with embodiments of the present system.
FIG. 3B is an illustration which shows a graph depicting a hospital clustering method performed in accordance with embodiments of the present system.
Figures 3C, 3D:
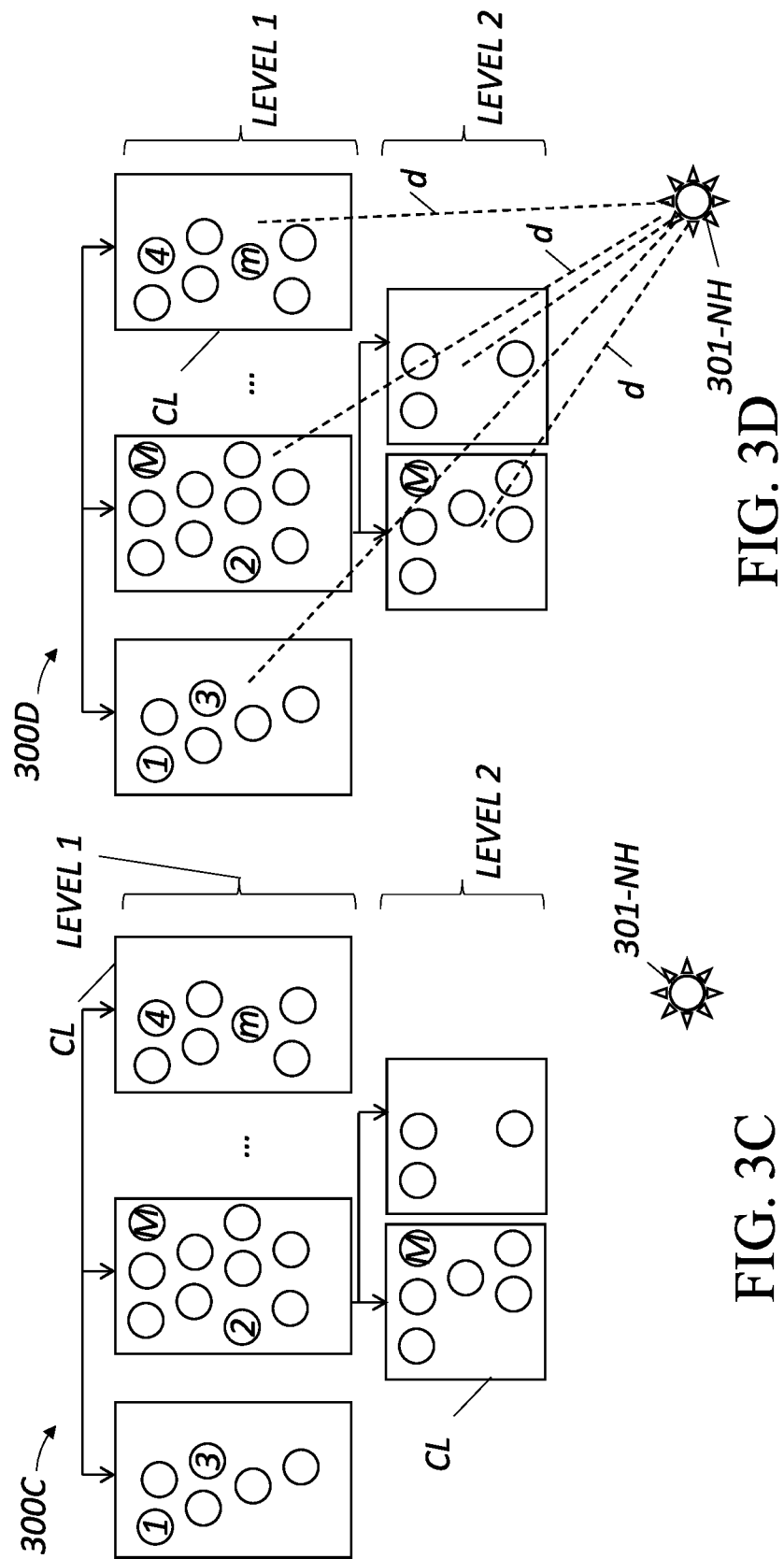
FIG. 3C is an illustration which shows a graph depicting a hospital clustering method performed in accordance with embodiments of the present system.
FIG. 3D is an illustration which shows a graph depicting a hospital clustering method performed in accordance with embodiments of the present system.
Figures 3E, 3F:
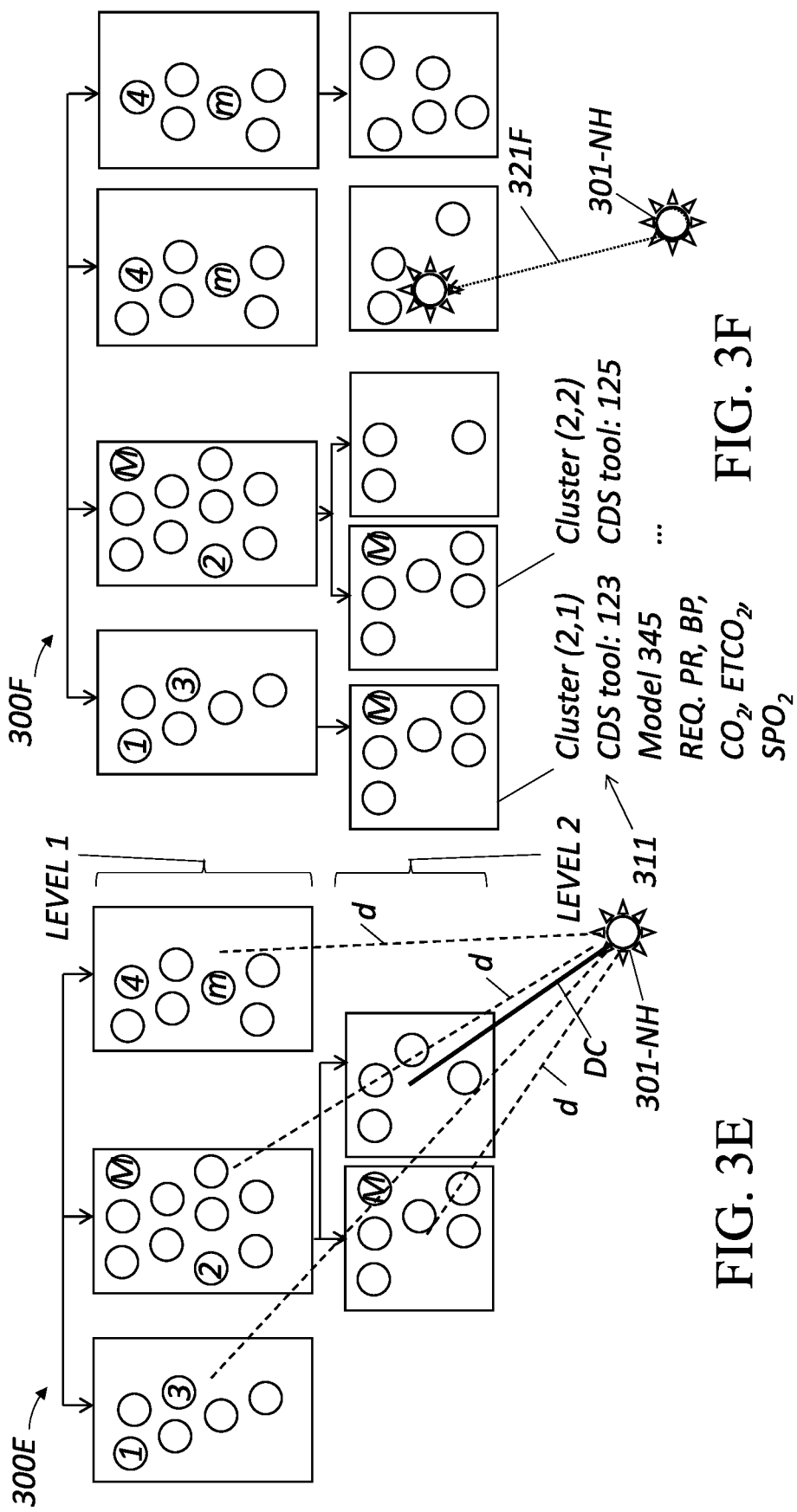
FIG. 3E is an illustration which shows a graph depicting a hospital clustering method performed in accordance with embodiments of the present system.
FIG. 3F is an illustration which shows a graph depicting a hospital clustering method performed in accordance with embodiments of the present system.

Methods of operation in accordance with embodiments of the present system will now be discussed with reference to FIGS. 2 through 3F wherein: FIG. 2 is an illustration which shows a functional flow diagram 200 performed by a process in accordance with embodiments of the present system; FIG. 3A is an illustration which shows a graph 300A depicting a hospital clustering method performed in accordance with embodiments of the present system; FIG. 3B is an illustration which shows a graph 300B depicting a hospital clustering method performed in accordance with embodiments of the present system; FIG. 3C is an illustration which shows a graph 300C depicting a hospital clustering method performed in accordance with embodiments of the present system; FIG. 3D is an illustration which shows a graph 300D depicting a hospital clustering method performed in accordance with embodiments of the present system; FIG. 3E is an illustration which shows a graph 300E depicting a hospital clustering method performed in accordance with embodiments of the present system; and FIG. 3F is an illustration which shows a graph 300F depicting a hospital clustering method performed in accordance with embodiments of the present system.

Referring back to FIG. 2, the process 200 may be performed using one or more controllers communicating over a network and may obtain information from, and/or store information to, one or more memories which may be local and/or remote from each other. The process 200 may include one of more of the following steps. In accordance with embodiments of the present system, the steps of the process 200 may be performed using a controller operating in accordance with embodiments of the present system (i.e., a controller programmed or otherwise configured in accordance with embodiments of the present system, thereby becoming a special purpose processor and/or circuit). Further, one or more of these steps may be combined and/or separated into sub-steps, as may be desired. Further, one or more of these steps may be skipped or the order between steps may be changed depending upon system settings operating in accordance with embodiments of the present system.

With reference to process 200, in operation, the process may start during act 201 and then proceed to act 203 wherein the process may initialize in accordance with one or more operating settings as may be input by a user (e.g., in real time) or may be obtained from a memory of the system such as from the SSI. The one or more operating settings may, for example, include information related to initialization and/or default settings, etc. The default settings may be set, reset, and/or updated by the system and/or operator and/or may be stored in the SSI. Accordingly, the controller may obtain the SSI from a memory of the system and/or may render information requesting input by the operator of one or more operating settings, depending upon system settings, such as may be stored in the SSI.

It is envisioned that the SSI may include information identifying one or more of a target patient population (TPP), selected physiological measurements of interest (e.g., SMs), identities (IDs) of hospitals (hospital ID) forming one or more hospital groups which may form an initial hospital group (IHG), etc. This group may be defined by a user of the system and may be stored in the SSI.

The IHG may define an initial group of hospitals from which EHRs may be obtained. For the sake of clarity, in the present embodiments each of these hospitals may be assumed to vary along dimensions including size, facilities, protocols, and healthcare processes specialization, etc., and may employ different clinical protocols such that care practices for the same patient may be assumed to vary in one or more of the hospitals such as having different patient data availability and/or patient data acquisition intervals. The IHG may include IDs (e.g., hospital IDs) or other identifying information of each of its the member hospitals, one or more of which may be selected by the system and/or user. The IHG is illustrated with reference to FIG. 3A wherein hospitals 301-1 through 301-M (where M is an integer) form the IHG and are shown within a box 303.

The TPP may define a target patient population such as mechanically ventilated patients (MVPs) (as used in the present embodiments). The TPP may be set by the system and/or user. For example, the user may select the TPP from a menu, for example adult MVPs (>18 yr) that are on a mechanical ventilation for more than 48 hours as a prolonged mechanical ventilation increases the risk of ventilator-associated events (VAE)s and the user is interested in estimating the risk of these events including VAP.

The SMs may limit an extraction and may correspond with the PMs as described above. For example, blood pressure and pulse rate are each physiological measurements which, when selected, the process may limit the extraction to these SMs. In contrast, when blood pressure (BP) is selected as an SM and pulse rate (PR) is not, the process may limit the extraction to blood pressure and not pulse rate. In some embodiments, it is envisioned that the SMs may include as a specific set of pre-specified measurements by type as may be defined by, for example, a specialist or a clinical guideline, etc., and which may be stored in the SSI. Accordingly, in some embodiments, the SMs may include types as may be selected by a user (e.g., the specialist, a clinician, etc.), and/or may be selected by the system (e.g., from a clinical guideline, etc.) and stored in the SSI. Once obtained, the SMs may be stored in the SSI for later use such as for use during an extraction. Types of SMs may correspond with types of physiological measurements and, for example, may include lab work, images, etc. For example, in the present embodiments, it is envisioned that lab work may include white blood cell counts, glucose level, lactate, etc., and images may include X-ray, computed tomography (CT) scans, ultrasound, etc. After completing act 203, the process may continue to act 205.

During act 205, the process may request and/or acquire an EHR dataset ($EHR_{DS}$) corresponding to the TPP for each hospital which belongs to the IHG. Accordingly, the $EHR_{DS}$ may include the EHRs and corresponding EMRs for each patient of the TPPs at each of the corresponding hospitals (e.g., 101-x) which belong to the IHG. In some embodiments, the TPP may be set to all patients in which case the $EHR_{DS}$ may include EHRs for all patients of each hospital of the IHG. In some embodiments, the $EHR_{DS}$ may be obtained from each hospital of the IHG while in others the $EHR_{DS}$ may be obtained from a central database which may store the $EHR_{DS}$. Accordingly, if the $EHR_{DS}$ is to be obtained from each hospital of the IHG, the process may communicate with each of the hospitals (e.g., see 101-x) of the IHG and query or otherwise request each hospital's respective EHRs that correspond to the TPP. In some embodiments, it is envisioned that the process may communicate with the central database which may store at least the $EHR_{DS}$ to request and acquire the $EHR_{DS}$ from this central database in accordance with the TPP. When the TPP includes all patients (or is not defined), the $EHR_{DS}$ may include all available EHRs and their corresponding EMRs. In a case wherein the TPP includes only certain defined patients (e.g., patients receiving mechanical ventilation therapy, etc.), each hospital of the IHG may provide the $EHR_{DS}$ that may include EHRs that correspond to the TTP.

It is envisioned that the $EHR_{DS}$ may be acquired and/or updated by the system at periodic or non-periodic intervals as may be set by the SSI and/or a user of the system. It is envisioned that the SSI may further include information related to communication methods that may be employed to acquire the $EHR_{DS}$. The EHRs in the $EHR_{DS}$ may be anonymized to maintain patient anonymity, if desired. In some embodiments, EHRs for each TPP may be bound within a selected time frame (e.g., a one-year period, a selected date range, a specific time, etc.) as may be selected by the user and/or system and which may be stored in the SSI.

Referring back to FIG. 2, after completing act 205, the process may continue to act 207.

During act 207, the process may, using any suitable extraction algorithm, perform an extraction process to extract EMR data for the target patient population. Further, during act 207, the EMR data may be processed by cleaning/correcting charting errors, applying plausibility filters for physiological measurement, for example, from the EMRs of the $EMR_{DS}$ (e.g., limited to mechanically ventilated patients (MVPs) in the present embodiments as an example) in accordance with at least the SM and may form a corresponding target patient cohort data set ($TPC_{DS}$) including the EMRMFs for each corresponding hospital of the IHG. The SM may be set such that the process may limit the extraction to a specific set of pre-specified measurements defined by the SM. For example, the SM may be set such that these pre-specified measurements may include measurements that may be provided by a user, such as a specialist, may be extracted from a clinical guideline, or may be set to all such that the process may extract all the measurements available for the patients of the TPP such as demographics, comorbidities, vitals, labs, interventions, etc. For the sake of clarity, in the present embodiments the SM may be assumed to be set to X-ray, $CO_2$, $SpO_2$, pulse rate, and blood pressure to limit the extraction to these measurements and intervals of these measurements. It should be appreciated that reference will be made to EMRs rather than EHRs for the sake of simplicity though may also be similarly applied to EHRs. In accordance with embodiments, acts 205, 207 may be combined together and performed during a single act in that, in accordance with this embodiment, one might acquire the $EHR_{DS}$ when extracting the EMR data for the target patient population. After completing act 207, the process may continue to act 209.

During act 209, The process may obtain the $TPC_{DS}$ and may, using any suitable feature computation algorithm, compute features at the patient level capturing a time interval between each subsequent record for each type of measurement (e.g., X-ray, $CO_2$, $SpO_2$, pulse rate, and blood pressure in the current embodiments) defined by the SM and form corresponding patient level features (e.g., see, PLFs-1 through PLFs-3, generally PLFs, FIG. 1). These time intervals may be represented by ($\Delta t_i$) and may be referred to as patient-level time intervals. Thus, the PLFs may include information related to the patient-level time intervals ($\Delta t_i$) between subsequent recordation entries (REs), and/or their corresponding frequencies ($f_{ti}=1/\Delta t_i$), for each of the corresponding SMs (e.g., $CO_2$, $SpO_2$, pulse rate, blood pressure, in the present embodiments) which may be extracted from the $TPC_{DS}$ for each patient of each hospital of the IHG (e.g., 101-$x$).

Figure 4:
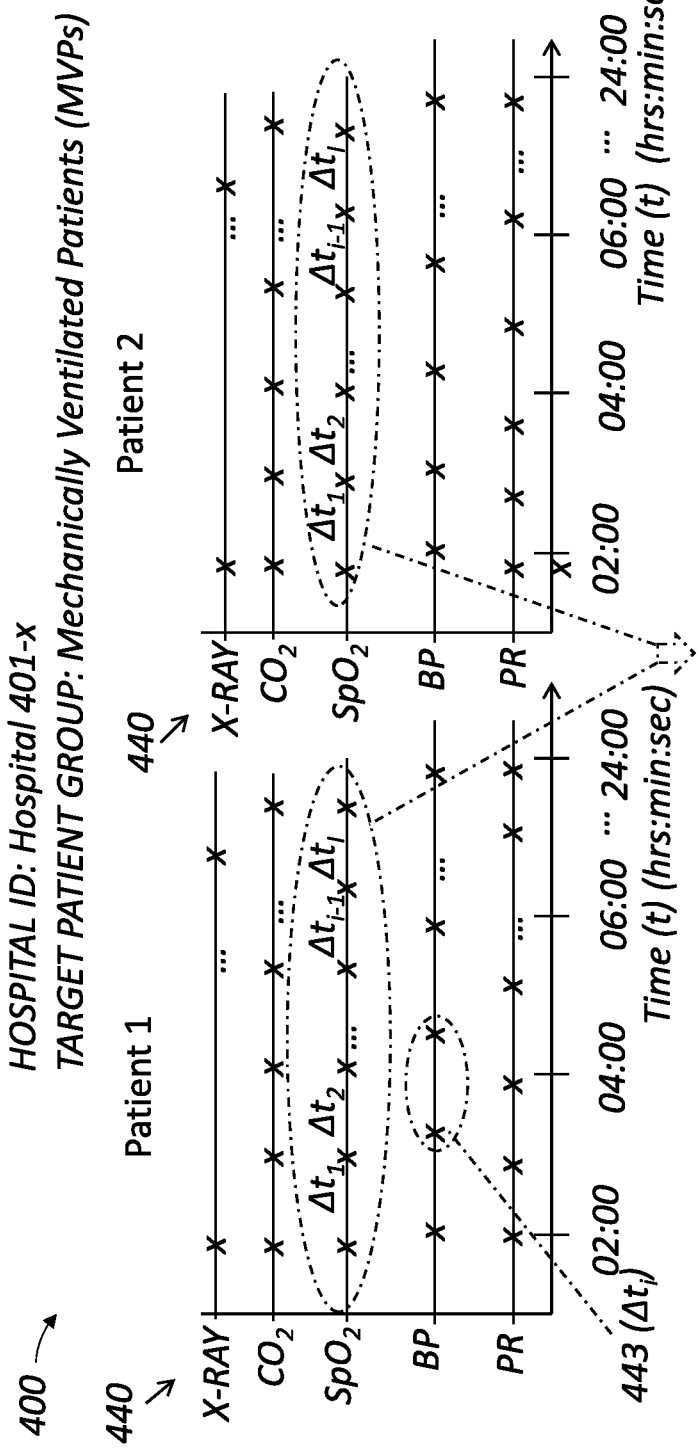
FIG. 4 which shows a graph which illustrates record entries for corresponding selected physiological measurements (SMs) with respect to time (t) for first and second patients of a target patient population (TPP) of a hospital in accordance with embodiments of the present system.

It is envisioned that depending upon embodiments, the process may determine the patient-level time intervals (e.g., $\Delta t_i$) and/or frequency of measurements ($f_{ti}=1/\Delta t_i$)) for each of the corresponding SMs (e.g., PR recorded once every three minutes, etc.) rather than actual measurement values for each of the corresponding SMs (e.g., pulse rate=60 bpm, etc.). This may assure anonymity of data during further processing and further, ensures that the clustering is oblivious to actual patient status captured in the values of the measurements. The system may be operative using the patient-level time intervals ($\Delta t_i$) and/or their corresponding frequencies ($f_{ti}=1/\Delta t_i$). A graphical depiction of this is illustrated in FIG. 4 which shows a graph 400 which illustrates record entries for corresponding SMs 440 with respect to time (t) for first and second patients (e.g., patient 1 and patient 2, respectively) of a TPP of a hospital 401-$x$ in accordance with embodiments of the present system. For each of the SMs, record entries are illustrated using "Xs" to indicate their time of recordation in the EMR of the corresponding patient of the first and second patients. Once a plurality of record entries are determined for an SM, the process may determine the patient-level time intervals $\Delta t_i$ (where i is an integer that may take a value from 1 through I) (e.g., 443) between subsequent record entries of the plurality of determined record entries as shown with reference to the $SpO_2$ SM.

The process may then determine the corresponding frequencies of measurement $f_{ti}=1/\Delta t_i$ for each of the corresponding patient-level time intervals ($\Delta t_i$) and/or may determine the frequencies of measurement $f_{ti}$ directly, for each of the patients of each hospital. The process may then, determine the PLFs for each of the corresponding patients (e.g., patient 1 and patient 2, in the present examples) as shown and form a corresponding PLF for the corresponding patient. The PLF may be a vector. For example, sample PLFs determined by the system for patient 01 and patient 02 are shown. For the sake of clarity, it will be assumed that measurements (e.g., blood pressure, etc.) may be obtained and recorded substantially synchronously with each other. For example, if a clinician observes the blood pressure of a patient and then enters this pressure for recordation at a recordation time, it will be assumed that that the observation time and recordation time are substantially the same or the record entries may include information on the time a measurement was taken, such as blood pressure. Further, the record entries may be collected over a threshold time period as may be set forth by the user and/or system or clinical protocol in use at a hospital and may be stored in the SSI.

Referring back to FIG. 2, after completing act 209, the process may continue to act 211 where the process may obtain the PLFs and compute features at the hospital level therefrom using any suitable feature extraction algorithm operating in accordance with embodiments of the present system. For example, for a hospital and a measurement pair (the pairing of the hospital with the associated measurement), the hospital-level features are a high-level representation (e.g., mean interval) of a target patient-level feature (e.g., $SpO_2$ intervals) for the TPP in a hospital. In accordance with embodiments of the present system, the process may compute statistics descriptive of the distribution of patient-level intervals (e.g., median, 25% percentile, 75% percentile, etc.) for that measurement (e.g., SM) in the corresponding hospital. The process may do this for each of the hospitals of the IHG such that each hospital may be represented in terms of the computed hospital-level features which may form a corresponding hospital-level feature (HLF) data set (e.g., see, HLF 127, FIG. 1). Each of the hospitals of the IHG may then be represented in terms of the computed hospital-level features. The computed hospital level features thus, may include statistics descriptive of the distribution of the captured time intervals for each of measurement(s) defined by the SM in the computed patient level features. After completing act 211, the process may continue to act 213.

During act 213, the process may perform a dimensional reduction (DR) on the HLF data set. Accordingly, the HLF data set may be processed to project each of the hospitals of the IHG into a low-dimensional space (LDS) using conventional dimensionality reduction techniques (e.g., principal component analysis (PCA) algorithms) and/or the like. In other words, the method/system may process HLF data set to transform data within it from a high-dimensional space into a low[er]-dimensional space and form a corresponding DR data set (DRDS) (e.g., see, FIG. 1, DRDS 129). At this time the EMR profile of the hospitals of the IHG is formed. After completing act 213, the process may continue to act 215.

During act 215, the process cluster the hospitals of the IHG. Accordingly, the process may receive the DRDS and process it using any suitable clustering technique(s) which may be operative to cluster the hospitals into a plurality of clusters (e.g., clusters of the IHG as seen in FIGS. 3A through 3E) and form corresponding cluster information (CLI). With regard to the clustering, it is envisioned that the process may search for clusters of similar hospitals in the previously determined low-dimensional space (LDS) using any suitable clustering technique(s) such as k-means, hierarchical (as will be shown and described below with respect to FIGS. 3A through 3F), and/or spectral clustering, and may evaluate the goodness of clustering using measures such as silhouette coefficients, etc.

In accordance with embodiments, the clustering may be adjusted. For example, the adjustment may be performed periodically, and/or may be performed at set intervals. In addition, or alternatively, the cluster compositions may be adjusted whenever a new hospitals is present and needs to be assigned either to the closest existing cluster or may form a new cluster if none of the existing clusters are similar to the newly observed hospital as is illustrated in FIGS. 3D, 3E, 3F.

In the case of hierarchical clustering, a level of hierarchy may be selected (by the system and/or user) for which clusters are defined for downstream prediction tasks. Selecting clusters deeper in the clustering hierarchy results in more homogenous clusters, while clusters at lower levels of hierarchy will typically have a larger amount of variability. The process may also be operative to train models in accordance with user and/or system settings as may be set forth in the SSI. Models trained on lower hierarchy levels might be more generalizable compared to those trained on clusters at deeper levels of hierarchy. However, this depends on the specific data driven task as may be set forth by the user and/or system settings (e.g., as may be set forth in the SSI). Nevertheless, the hierarchy of clusters provides the flexibility to form clusters as they fit the downstream prediction tasks as will be explained with reference to act 231 below. After completing act 215, the process may continue to act 217 which begins the process for adjustment of clusters once a new hospital is presented in accordance with embodiments of the present system.

During act 217, the process may determine whether a new hospital (NH) is presented. Accordingly, if it is determined that a NH is presented, the process may continue to act 219. However, if it is determined that a NH is not presented, the process may repeat act 217 or alternatively, continue to act 227. The process may determine that a NH is presented upon selection of a NH by a user or when a NH is presented by the system. The NH may be assumed to be similar to the hospitals of the IHG (e.g., may be a cardiac care hospital) but is not currently part of the IHG or may be processed without assumptions about the similarity between prior hospitals and the NH.

During act 219, the process may generate an EMR profile for the NH. The process may do this similarly to the methods employed to determine an EMR profile of the hospitals of the IHG. For example, the process may obtain an $EMR_{DS}$ of the NH from the memory and thereafter repeat acts 207 through 213 using this $EMR_{DS}$ for the NH to generate the EMR profile for the NH similarly to the methods employed to generate the EMR profiles for each of the hospitals of the IHG. The resulting high-dimensional EMR profile for NH may then embedded in the low-dimensional space created previously for IHG in 213. After completing act 219, the process may continue to act 221.

During act 221, the NH may be compared with the existing clusters of hospitals of the IHG based upon their EMR profile. This is graphically illustrated with reference to FIG. 3D and the corresponding description. After completing act 221, the process may continue to act 223.

During act 223, the process may compare the EMR profile of the NH to the EMR profile of the hospitals of the IHG to determine whether the NH is within a threshold distance (e.g., d is less than or equal to the threshold distance) to the closest existing cluster of the clusters of the IHG. For example, the process may determine the Euclidean distance between the NH (e.g., see, 301-NH) and the existing cluster heads (or cluster centroids that were previously determined during act 215) of the hospitals of the IHG. Graphically, this may be illustrated as shown in FIG. 3D wherein distances between the NH 301-NH and the cluster centroids are illustrated by dotted lines d. When the NH is within a threshold distance to the closest existing cluster of the clusters of the IHG, the process may continue to act 225. However, if it is determined that the NH is not within a threshold distance (e.g., d is greater than or equal to the threshold distance) to the closest existing cluster of the clusters of the IHG, the process may continue to act 228.

During act 225 (when the NH is within the threshold distance), the process may then assign the NH to the closest hospital (e.g., see, FIG. 3E). In this case, it was determined that NH was close (e.g., within the threshold distance) to the nearest existing cluster of the clusters of the IHG (distance to the closest cluster is highlighted as a continuous line in FIG. 3E). The threshold distance may be defined as a minimum neighborhood distance, which for example may be set to the largest within-cluster distance (e.g., distance from cluster members to the cluster head/centroid) for the existing clusters of the IHG. Alternatively, the threshold distance may be set by the user or system to another value.

During act 225, the process may assign the NH to this closest existing cluster (e.g., see, FIG. 3E). After completing act 225, the process may continue to act 227.

During act 228 which is performed when the NH is not within the threshold distance, the process may form a new cluster for the NH to account for the distinctiveness of the NH. In this case, no cluster of the hospitals of the IHG are close enough to the NH. After completing act 228, the process may continue to act 229 where the process may assign the NH to the new cluster that was created for the NH (e.g., see, FIG. 3F) and may thereafter continue to act 227.

Thus, during acts 217 through 227, the NH may be compared with the existing clusters of hospitals (e.g., the clustered IHG) based on their respective EMR profiles and the new hospital (e.g., FIG. 3C, 301-NH) may be either assigned to: a cluster whose members are determined to have the most similar profiles (close enough to) to that of the new hospital (e.g., FIG. 3E); or to a new cluster, if no cluster is identified as close enough to (e.g., within the threshold distance to) the new hospital (e.g., FIG. 3F, 301-NH). In the latter case, the system may create a new cluster to account for this new hospital (e.g., FIG. 3F, 301-NH) that is distinct. The similarity to clusters may be measured using Euclidean distance between the new hospital and different cluster heads (or cluster centroids). The new hospital will be assigned to the cluster with the shortest distance. A threshold may be set to define the minimum neighborhood distance (e.g., a threshold neighborhood distance) for a cluster. If the distance between a hospital and the existing clusters is larger than the minimum neighborhood distance, then the new hospital cannot be assigned to any cluster and a new cluster will be formed to host the new hospital. The minimum neighborhood distance may be set to the largest within-cluster distance (distance from cluster members to the cluster head/centroid) for the existing clusters; alternatively, it may be set by the user.

At this point the hospitals (e.g., the hospitals of the IHG and the NH) may be clustered into identified clusters and the process may perform Hospital-Aware CDS design and/or adaption in accordance with embodiments of the present system. For example, the identified clusters may then be used for downstream patient-level prediction tasks such as may be explained below with reference to act 227 below.

The clustering process in accordance with embodiments of the present system may be illustrated in further detail with reference to FIGS. 3A through 3F which graphically illustrate hierarchical clustering performed in accordance with embodiments of the present system using a top-down approach (e.g., divisive, using levels 1 through 3 as shown) as opposed to a bottom-up approach (agglomerative) for the sake of clarity although either approach may be used by the process as may be selected by the system and/or user.

With reference to FIG. 3A, an IHG may include hospitals 301-1 through 301-M (generally 301-x) which are depicted as circles within box 303 which surrounds the IHG to be categorized in accordance with embodiments of the present system. Each of the hospitals 301-x of the IHG is to be categorized and is assumed to be different from each other. After clustering, each hospital 301-x may be represented based upon their corresponding hospital-level EHR data and is situated within a corresponding cluster or clusters (CL) on first and second hierarchical levels (e.g., level 1 and level 2, respectively). The hospitals 301-x which form a corresponding cluster (CL) may be situated within a corresponding box for the sake of clarity. Numbers within the circles depict an ID of the corresponding hospital 301-x for the sake of clarity only.

With reference to FIG. 3B, clusters may be incrementally broken into smaller clusters creating a hierarchy of hospitals 301-x based on their EHR data as shown in level 1 through level 3. This may be in response to a user input wherein, for example, a user changes SMs, etc. Alternatively, the hierarchy level and the number of clusters can be determined using goodness of clustering metrics such as silhouette coefficients and/or elbow method on the sum of squared errors (the square of the Euclidean distance of the point to its cluster head or cluster centroid). In this case, clusters are formed based on either a preset level on these metrics or by users inspecting the metrics and choosing a clustering results with a favorable goodness metric as it fits their needs. The level of hierarchy and the number of clusters may also be determined using goodness of clustering metrics.

With reference to FIG. 3C, when a new hospital (NH) 301-NH is presented to the system, the system may generate an EHR profile for this hospital using similar methods as those used to generate EHR profiles for the hospitals of the IHG. Then, with reference to FIG. 3D, the NH 301-NH is then compared with the existing clusters of hospitals based on their EHR profiles. As a result of this comparison, the system may determine whether the NH 301-NH is within a minimum neighborhood distance (e.g., which is a threshold distance as shown by dotted lines d) of a cluster with members. In other words, the system may determine whether there are any clusters with members that are close enough (e.g., within the minimum neighborhood distance) to the NH 301-NH. When it is determined that the NH 301-NH is within the minimum neighborhood distance of a cluster with members, the NH 301-NH may be assigned to that cluster which is a cluster whose members (e.g., hospitals) are determined to have the most similar profiles to that of the new hospital (NH 301-NH) as shown in FIG. 3E. The distance between the NH 301-NH may be calculated between the NH 301-NH and a centroid of a corresponding cluster or other select location of the corresponding cluster as illustrated by dotted lines d. With reference to FIG. 3E, the line DC is drawn to a cluster that the NH 301-NH may be determined to be closest to (e.g., within the minimum neighborhood distance). Accordingly, the system may then assign the NH 301-NH to this cluster. Thus, the NH 301-NH may be assigned to a cluster whose members have the most similar profiles to that of the NH 301-NH.

With reference to FIG. 3F, if it is determined that the NH 301-NH is not within the minimum neighborhood distance of a cluster with members, the system may then assign the NH 301-NH to a new cluster as illustrated by arrow 321F. Thus, as no cluster was identified as close enough (e.g., within the minimum neighborhood distance) to the NH 301-NH, the system may create a new cluster to account for the distinctiveness of the NH 301-NH and place the NH 301-NH within this cluster.

With reference back to FIG. 2, during act 227 the identified clusters are then used in downstream patient-level prediction tasks such as: (a) cluster membership can be used as a feature alongside other patient-level features for downstream prediction tasks; and (b) a dedicated model may be trained for each cluster (e.g., a cluster-specific model). After completing act 227, the process may continue to act 231 where the process ends.

In some embodiments, each hospital cluster may be characterized by a type and frequency of available physiological measurements (e.g., sensor data, lab work, images, etc.). A separate CDS tool may be built for each hospital cluster. The resulting models may be ranked based on their performance. Furthermore, the process may provide specifications for each cluster-specific model describing minimum input measurements (e.g., physiological measurements, etc.) required. As a result, a new hospital (NH) may have the option to select a model from a plurality of cluster-specific models based on the performance of these models, by adapting to the minimum input measurements required for that cluster-specific model. For example, if the selected model ($M_a$) requires measurement of $etCO_2$, then the process may inform the NH (e.g., via a rendering device of the system) that the NH will need to measure $etCO_2$ in order to use this selected model ($M_a$). The process may further set one or more therapeutic devices of the NH to settings of the selected model. The system may render the CDS tool and/or models in association with the cluster. For example, with reference to FIG. 3F, each cluster may include a menu-item 311 which may include a cluster ID (e.g., in (row, column) format as shown) and corresponding information such as CDS tool ID (e.g., CDS 123), models available (e.g., model 123), required physiological measurements (e.g., $SpO_2$, $CO_2$, $O_2$, $etCO_2$,), data acquisition frequency, time between repeat acquisitions of data, etc., selection of which may cause the system to render corresponding information. The menu-item 311 may be displayed in response to the selection of the corresponding cluster.

It is envisioned that in some embodiments the process may determine whether a set of required measurements (e.g., physiological measurements), for the selected model used by a hospital is missing (e.g., not being collected) and in the affirmative may render results of this determination (e.g., "$etCO_2$ is a required type of measurement that is not being collected or is not being collected at a given required interval—please correct") on a rendering device of the system. Conversely, if it is determined that a set of required measurements for the selected model used by a hospital is not missing (e.g., is present or collected), the process may render results of this determination (e.g., "$etCO_2$ is a being collected") on a rendering device of the system. The process may, depending upon settings, render results of determinations on a rendering device of the system such as a selected rendering device and/or may transmit information of determinations to a registered address associated with the hospital using the selected model as may be set in the SSI. For example, the process may notify a registered address (e.g., of a user associated with the hospital using the selected model) that the set of required measurements (e.g., for the current model that is being used) is missing and may provide an indication of what required measurements are missing (e.g., "$etCO_2$ is missing"). In accordance with embodiments of the present system, it is envisioned that in some embodiments all the cluster-specific models may be selected to be synchronously or serially deployed in a hospital. It is also envisioned that for every prediction task: 1) a model can be used based upon the availability of the data (e.g., which may form one or more physiological measurements of interest), or 2) a user or the system may select a model for prediction based upon available inputs (e.g., physiological measurements) that may be available at a corresponding hospital (e.g., the NHC). Moreover, it is envisioned that multiple cluster-specific models can be employed, and a final prediction may be an aggregate (e.g., an average prediction score) of individual cluster-specific predictions. In this embodiment, the variability in prediction can be captured by computing measures of dispersion (e.g., standard deviation, variance) or entropy of the individual predictions and used to report prediction uncertainty. This report (e.g., the prediction uncertainty) may then be rendered on a rendering device of the system for the convenience of one or more users. Further, the resulting prediction uncertainty can be used by embodiments of the system to qualify a valid prediction as the prediction with the least variation across different models.

It is envisioned that for every prediction, a risk score (e.g., the likelihood of developing a target infection) is accompanied with top 'n' features most salient for the prediction. The 'n' can be set by the user or otherwise is set to a suitable number such as five, depending upon system and/or user settings as may be set forth in the SSI. Furthermore, it is envisioned that at the same hospital, different models may be used in different intensive care unit (ICU) types and wards based on the availability of data (physiological measurements) that may be collected at different locations throughout the hospital and may be associated with these locations. Thus, it is envisioned that embodiments of the system may be suitable for intra-hospital as well as inter-hospital use as may be set by the system and/or user and may be set forth in the SSI.

Accordingly, embodiments of the present system may present a hospital grouping approach based on the type of physiological measurements and their frequencies for a patient cohort of interest (e.g., mechanically ventilated patients). An exemplary embodiment provides a prediction of ventilator-associated pneumonia (VAP). The proposed hospital grouping results in a significant improvement in prediction performance.

Embodiments of the present system may be used with ventilator-associated event systems and methods and may present a generic approach as a pre-processing step for building suitable data driven CDS tools. Embodiments may provide for CDS tools and offerings based on complexity, performance, hospital and EMR integration requirements, and supply a pool of hospital clients by offering CDS tools customized for the hospital of choice such as a corresponding hospital client such as the NH. This is particularly important to improve fairness in CDS tools, by ensuring for instance that hospitals with lower resources are not disadvantaged only because they don't have certain measurement devices or nursing staff to make a target measurement at the frequency done at bigger teaching hospitals. As such the proposed present system enables creating CDS tools tailored for different classes of hospitals, that may for example be different in teaching status, size, and healthcare processes and facilities.

Embodiments of the present system may provide a hospital categorization framework to group hospitals into clusters of similar hospitals based on their respective EMR data. The EMR data reflect the actual practice and documentation of care at different hospitals. The EMR-derived features representing data availability can be augmented with other high-level hospital characteristics (e.g., number of beds, ICU types available in the hospitals) to form hospital clusters.

The identified clusters may then be used by the system to create CDS tools tailored to each cluster of hospitals and provide these tools to a user for operation. The hospital clustering may be re-examined periodically to account for any changes in care practice and documentation that might trigger the need for retraining CDS tools. Accordingly, embodiments of the present system may constantly monitor for changes in physiological measurements (e.g., in time, type) that extend beyond corresponding threshold changes. In this way, the present system may capture changes in hospital-level practices.

Accordingly, embodiments of the present system will help improve the quality of CDS tools and in turn, customer satisfaction by providing hospital-aware CDS tools. The proposed hospital groupings may be flexible and can be used to create a new grouping for every new CDS tool based on the medical condition it addresses (e.g., VAP, etc.). While hospital groupings are illustratively discussed, it is readily appreciated that the same processes may be utilized to make other clusters such as departmental clusters to ensure that CDS tools are tailored to different departments even within a hospital which may have different protocols for different measurements. In this way, the CDS tool may be tailored to the departments and may provide guidance as to which department is most suitable for a given patients' care needs.

Test Results

In an experiment across 292 hospitals (e.g., N=292) in the eICU dataset, the process identified four clusters of hospitals using the approaches set forth by embodiments of the present system. The identified clusters were then used in a downstream VAP prediction task. On average, cluster-specific models improved the area under the curve receiver operator characteristic (AUC ROC) by 7% as compared with a model trained without regard to inter-hospital differences and associated hospital clusters. It has also been observed that within-cluster performance is significantly higher as compared with out-of-cluster performance. On average, the AUC ROC for within-cluster samples is 12% higher than the AUC ROC on the out-of-cluster samples for the VAP prediction task.

In another experimental use case for VAP prediction, the system identified 4 clusters of hospitals based on their respective EMR data and developed cluster-specific predictive models. The resulting cluster-specific models significantly outperform (up to 10% improvement in AUC ROC) a model that was built without regard to inter-cluster differences. It has also been observed that cluster-specific models perform poorly on out-of-cluster hospitals with different sets of features deemed to be salient for different clusters. This observation indicates significant between-hospital differences and highlights the importance of building models tailored to the specifics of each type of hospital as provided by embodiments of the present system.

In some embodiments, it is envisioned that the system may store and/or render a list of selections for a user to enter information such as a TPP, etc. For example, FIG. 5 shows a graphical user interface (GUI) 500 generated and rendered by the system in accordance with embodiments of the present system. It is envisioned that in some embodiments, the system may render a request for the user to enter a target patient pool to be selected as the TPP which may be entered directly or selected from a list of available TPPs (501). Similarly, the system may render a list of one or more physiological measurements that may be selected by the user and set by the system as SMs when selected. This list may correspond with the selected TPP and may include, for example, imaging selections 505 and vitals selection 507. The TPP and SMs may then be used by the process for the extraction in accordance with embodiments of the present system. For example, to select a TPP, the user may select one or more therapies from the list of therapies, (e.g., VAP, etc.) and the system may determine a corresponding TPP. For example, with reference to FIG. 1, the controller 140 may render (e.g., on a rendering device of the system such as the display 146) a request for the user to select the TPP and/or SMs from a corresponding list of available TPPs and SMs to be employed by the process such as is shown. The user may then interact with a user interface of the system, such as a touchscreen display to enter selections to be used by the process. The system may render a list of new hospitals (NHs) (509) for selection by the user. The system may further render feature determination selections (511) and response to selection of manual entry. The system may provide an entry area for the user to enter or select envisioned features for the NH such that models may be run using these features and/or downstream tasks and/or CDS tools may be built, selected, and/or run depending upon system settings. In response to the selection of the automatic feature determination, the system may extract features for the selected NH similarly to the methods used to select features of the hospitals 101-x of the IHG is selected.

Figure 6:
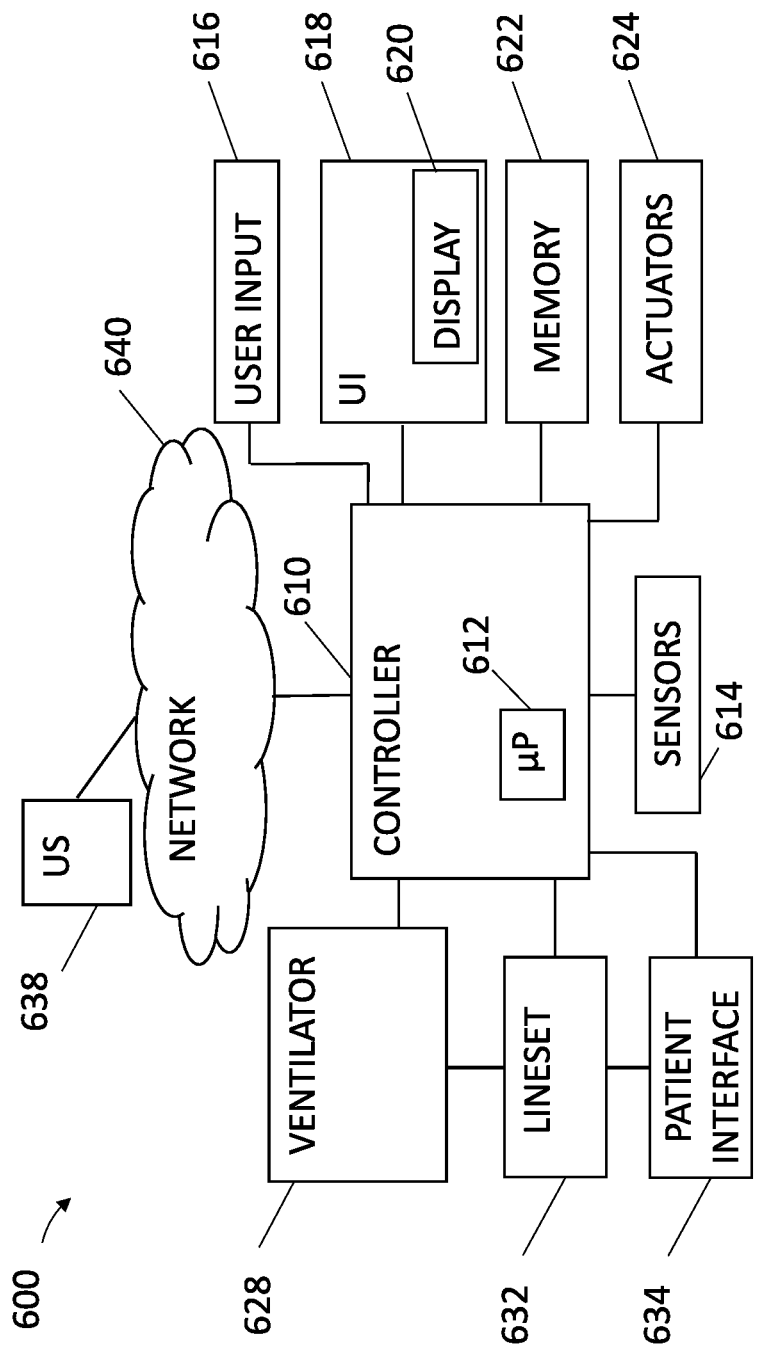
FIG. 6 shows a block diagram of a portion of a system in accordance with embodiments of the present system.

FIG. 6 shows a block diagram of a portion of a system 600 (hereinafter system 600 unless the context indicates otherwise) in accordance with embodiments of the present system. The system 600 may include one or more of: a controller 610, sensors 614, a user input interface 1316, a user interface (UI) 618, a memory 622, actuators 624, a ventilator 628, a line set (e.g., a patient line set) 632, a patient interface 634, a network 640, and an optional a user station (US) 638 each of which may be coupled to and/or communicate with each other using any communication method or methods such as wired, optical, flow, and/or wireless communication methods. The system 600 may be operative under the control of the controller 610.

The US 638 may include any suitable user station such as a smart phone or the like that may be configured to communicate with other portions of the system 600 such as the controller 610 via any suitable communication method or methods such as via the network 640.

The controller 610 may include one or more logic devices such as a microprocessor (μP) 612 and may control the overall operation of the system 600. It would be appreciated that in some embodiments the controller 650 may include digital and/or analog control circuitry.

It is envisioned that one or more portions of the system 100 such as the controller 610 may be operationally coupled to the memory 622, the user interface (UI) 618 including a rendering device such as the display 620, the sensors 614, and the user input interface 616, the actuators 624, the line set 632, the patient interface 634, the network 640, and the US 638.

The memory 622 may be any type of device for storing application data as well as other data related to the described operation such as application data, SSI, EHRs, EMRs, operating parameters, CDS tools, etc. The application data, SSI, operating parameters, CDS tools, etc., may be received by the controller 610 for configuring (e.g., programming) the controller 610 to perform operation acts in accordance with the present system. The controller 610 so configured becomes a special purpose machine particularly suited for performing in accordance with embodiments of the present system.

The controller 610 may render content, such as still or video information, on a rendering device of the system such as on the display 620 of the UI 618. This information may include information related to operating parameters, instructions, feedback, and/or other information related to an operation of the system or portions thereof such as SSI or portions thereof, cluster information, CDS tools, etc.

The sensors 614 may be situated at one or more portions of the system and may sense related parameters, form corresponding sensor information, and provide this sensor information to the controller 610 for further processing such as for forming EHRs, cluster information, and CDS tools. For example, the sensors 614 may include sensors such as image and physiological sensors which may form corresponding sensor information (e.g., image, gas flow, gas pressure, etc.) and provide this information to the controller 610 for further analysis. The sensors 614 may be distributed throughout the system.

The user input interface 616 may include a keyboard, a mouse, a trackball, or other device, such as a touch-sensitive display, which may be separate or part of a system, such as part of a laptop, a personal digital assistant (PDA), a mobile phone (e.g., a smart phone), a smart watch, an e-reader, a monitor, a smart or dumb terminal or another device for communicating with the controller 610 via any operable link such as a wired and/or wireless communication link. The user input interface 616 may be operable for interacting with the controller 610 including enabling interaction within a UI 618 as described herein. Clearly the controller 610, the sensors 614, the user input interface 616, the user interface (UI) 618, the memory 622, the actuators 624, the line set (e.g., a patient line set) 632, the patient interface 634, the network 640, and the optional a user station (US) 638 may all or partly be a portion of a computer system or other device.

The UI 618 may be operative to provide audio/visual feedback to the user of the present system and may inform the operator of operating parameters, operating states, etc. For example, the UI may render information indicative of clusters, SMs, CDS tools, hospital IDs, etc.

The methods of the present system are particularly suited to be carried out by a computer software program, such program containing modules corresponding to one or more of: the individual steps or acts described and/or envisioned by the present system. Such program may of course be embodied in a computer-readable medium, such as an integrated chip, a peripheral device or memory, such as the memory 624 or other memory coupled to the controller 610.

The program and/or program portions contained in the memory 622 may configure the controller 610 to implement the methods, operational acts, and functions disclosed herein. In this way, controllers of prior systems may be greatly improved providing increased accuracy of CDS provided treatment recommendations, greatly improved CDS tools, etc.

The memories may be distributed, for example between the clients and/or servers, or local, and the controller 610, where additional processors may be provided, may also be distributed or may be singular. The memories may be implemented as electrical, magnetic or optical memory, or any combination of these or other types of storage devices. Moreover, the term "memory" should be construed broadly enough to encompass any information able to be read from or written to an address in an addressable space accessible by the μP 612 of the controller 610. With this definition, information accessible through a network such as the network 640 is still within the memory, for instance, because the processor 612 may retrieve the information from the network 640 for operation in accordance with embodiments of the present system.

The controller 610 is operable for providing control signals and/or performing operations in response to input signals from the user input device 616 as well as in response to other devices of a network, such as the sensors 614 and executing instructions stored in the memory 622. The μP 612 may include one or more of: a microprocessor, an application-specific and/or general-use integrated circuit(s), a logic device, etc. Further, the μP 612 may be a dedicated processor for performing in accordance with the present system and/or may be a general-purpose processor wherein only one of many functions operates for performing in accordance with the present system. The μP 612 may operate utilizing a program portion, multiple program segments, and/or may be a hardware device utilizing a dedicated or multi-purpose integrated circuit.

The actuators 624 may, under control of the controller 610, control one or more valves, pumps, and/or motors of the system under the control of the controller 610. For example, the actuators 624 may include one or more valve actuators that may control the pressure and/or flow of a fluid such as air used by the system such as in the line set 632.

The ventilator 628 may include one or more valves, fans, and/or pumps that may be configured to supply a flow of air suitable for performing a given therapy such as VAP therapy in accordance with embodiments of the present system.

The line set 632 may couple the patient interface 634 to the ventilator 628 and may include any suitable air flow path or paths such as may be provided by one or more tubes, hoses, or the like. The line set 632 may further include one or more sensors (e.g., sensors 614), filters, and/or valves.

The patient interface 634 may include any suitable patient interface such as a mask, a tracheostomy coupling, and/or mouthpiece configured to be coupled to the line set 632. When coupled together, the patient interface 1334 and the line set 632 may form one or more of a mask circuit, a trach circuit, and/or a mouthpiece circuit. The patient interface 634 may form a non-invasive patient interface.

Hospitals vary in terms of facilities, services, and patients they provide care to. While there is a high-level categorization of hospitals, for example in terms of medical specialization (cardiac, respiratory), the actual inter-hospital differences in care practices are often not readily obvious. Such differences play a central role in the success of data-driven clinical decision support systems (CDS) yet are not adequately addressed by prior CDS systems resulting in deployment of CDS tools that are not suitable for a given hospital/application. Embodiments of the present system solves these problems in prior systems and presents a framework to automatically build a hierarchy of hospitals based on available measurements and their frequencies in electrical health records (EHR) or other hospital databases that host patient data. The proposed framework finds clusters of hospitals with similar hospitals grouped together in separate clusters. This grouping of hospitals allows 1) automatic inclusion/exclusion of hospitals for CDS development, and 2) building CDS tools tailored to different clusters of hospitals or alternatively, use cluster membership as an input to a single CDS tool. For a new hospital (NH) (e.g., that is not part of existing clusters of hospitals), the present system may present an approach to: a) automatically assign the hospital to the most similar cluster, and b) form a new cluster or hierarchy if the new hospital doesn't fit under the existing clusters of hospitals.

Accordingly, embodiments of the present system may provide data driven CDS tools that may detect, predict, and/or estimate an event or risk of an event in healthcare settings. Further variations of the present system would readily occur to a person of ordinary skill in the art and are encompassed by the following claims.

Finally, the above discussion is intended to be merely illustrative of the present system and should not be construed as limiting the appended claims to any particular embodiment or group of embodiments. Thus, while the present system has been described with reference to exemplary embodiments, it should also be appreciated that numerous modifications and alternative embodiments may be devised by those having ordinary skill in the art including using features that are described with regard to a given embodiment with other envisioned embodiments without departing from the broader and intended spirit and scope of the present system as set forth in the claims that follow. In addition, any section headings included herein are intended to facilitate a review but are not intended to limit the scope of the present system. In addition, the specification and drawings are to be regarded in an illustrative manner and are not intended to limit the scope of the appended claims.

In interpreting the appended claims, it should be understood that:
a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function;
e) any of the disclosed elements may be comprised of hardware portions (e.g., including discrete and integrated electronic circuitry), software portions (e.g., computer programming), and any combination thereof;
f) hardware portions may be comprised of one or both of analog and digital portions;
g) any of the disclosed devices, features and/or portions thereof may be combined together or separated into further portions unless specifically stated otherwise;
h) no specific sequence of acts or steps is intended to be required unless specifically indicated; and
i) the term "plurality of" an element includes two or more of the claimed elements and does not imply any particular range of the number of elements; that is, a plurality of elements may be as few as two elements and may include an immeasurable number of elements.

What is claimed is:
1. A clinical decision support (CDS) system, comprising:
at least one controller, the at least one controller including at least one microprocessor and being configured to communicate with a plurality of hospital servers, the at least one controller being further configured to:
extract, via the plurality of hospital servers, electronic health records (EHRs) of a plurality of hospitals of an initial hospital group (IHG) in accordance with at least one of a selected target patient population (TPP) and selected physiological measurements of interest (SMs) to form a target patient dataset;
compute patient level features of the target patient dataset capturing a time interval between each subsequent record for each of the measurements defined by the SMs;
compute hospital level features of the target patient dataset comprising statistics descriptive of the distribution of the captured time intervals for each of the measurements defined by the SM in the computed patient level features;
cluster the plurality of hospitals of the IHG in accordance with the computed hospital level features into a plurality of clusters (CL);
determine whether another hospital is within a threshold distance (d) to a closest one of the plurality of clusters;
place the other hospital in the closest cluster when it is determined that the other hospital is within the threshold distance to the closest one of the plurality of clusters; and place the other hospital in a new cluster of the plurality of clusters when it is determined that the other hospital is not within the threshold distance to the closest one of the plurality of clusters.

2. The CDS system of claim 1, wherein the at least one controller is further configured to create at least one CDS tool tailored to each cluster of the plurality of clusters and associating the CDS tool with the corresponding cluster of the plurality of clusters.

3. The CDS system of claim 2, wherein the at least one controller is further configured to render information related to the at least one CDS tool in association with the corresponding cluster of the plurality of clusters.

4. The CDS system of claim 1, wherein the at least one controller is further configured to render information related to required physiological settings corresponding to a selected model associated with a cluster.

5. The CDS system of claim 1, wherein the at least one controller is further configured to compare an EMR profile for the other hospital with that of an EMR profile of at least one of the hospitals of the IHG.

6. The CDS system of claim 1, wherein the at least one controller is further configured to determine physiological measurements available to the other hospital.

7. The CDS system of claim 6. wherein the at least one controller is further configured to compare the physiological measurements available to the other hospital with physiological measurements required by a model and render results of the comparison.

8. The CDS system of claim 6. wherein the at least one controller is further configured to render a plurality of models in association with each cluster on a display of the system for selection by a user.

9. A clinical decision support (CDS) system, comprising:
at least one controller, the at least one controller including at least one microprocessor and being configured to communicate with a plurality of hospital servers, the at least one controller being further configured to:
receive selections corresponding to selected physiological measurements of interest (SMs) and a selected target patient population (TPP);
extract, via the plurality of hospital servers, electronic health records (EHRs) of a plurality of hospitals of an initial hospital group (IHG) in accordance with at least one of a selected TPP and SMs to form a target patient dataset;
compute patient level features capturing a time interval between each subsequent record for each measurement defined by the SMs;
compute hospital level features comprising statistics descriptive of the distribution of the captured time intervals for each of the measurements defined by the SM in the computed patient level features;
cluster the plurality of hospitals of the IHG in accordance with the computed hospital level features into a plurality of clusters (CL);
determine whether an other hospital is within a threshold distance (d) to a closest one of the plurality of clusters;
place the other hospital in the closest cluster when it is determined that the other hospital is within the threshold distance to the closest one of the plurality of clusters; and
place the other hospital in a new cluster of the plurality of clusters when it is determined that the other hospital is not within the threshold distance to the closest one of the plurality of clusters.

10. The CDS system of claim 9, wherein the at least one controller is further configured to create at least one CDS tool tailored to each cluster of the plurality of clusters and associate the CDS tool with the corresponding cluster of the plurality of clusters.

11. The CDS system of claim 10, wherein the at least one controller is further configured to render information related to the at least one CDS tool in association with the corresponding cluster of the plurality of clusters.

12. The CDS system of claim 9, wherein the at least one controller is further configured to render information related to required physiological settings corresponding to a selected model associated with a cluster.

13. The CDS system of claim 9, wherein the at least one controller is further configured to compare an EHR profile for the other hospital with that of an EMR profile of at least one of the hospitals of the IHG.

14. The CDS system of claim 9, wherein the at least one controller is further configured to determine physiological measurements available to the other hospital.

15. The CDS system of claim 14. wherein the at least one controller is further configured to compare the physiological measurements available to the other hospital with physiological measurements required by a model and render results of the comparison.

16. The CDS system of claim 14. wherein the at least one controller is further configured to render a plurality of models in association with each cluster on a display of the system for selection by a user.

17. The CDS system of claim 9, further comprising a display coupled to the controller, wherein the at least one controller is further configured to control the display to render a graphical user interface (GUI) including selection items for the user to select the selections corresponding to selected physiological measurements of interest (SMs) and a selected target patient population (TPP) from a user.

18. A clinical decision support (CDS) system, comprising:
at least one controller, the at least one controller including at least one microprocessor and being configured to communicate with a plurality of hospital servers, the at least one controller being further configured to:
compute patient level features capturing a time interval between each subsequent record for each measurement defined by selected physiological measurements of interest (SMs) from electronic health records, extracted via the plurality of hospital servers, of a target patient population (TPP) of a plurality of hospitals of an initial hospital group (IHG);
compute hospital level features comprising statistics descriptive of the distribution of the captured time intervals for each of the measurements defined by the SM in the computed patient level features;
cluster the plurality of hospitals of the IHG in accordance with the computed hospital level features into a plurality of clusters (CL);
determine whether an other hospital is within a threshold distance (d) to a closest one of the plurality of clusters;
place the other hospital in the closest cluster when it is determined that the other hospital is within the threshold distance to the closest one of the plurality of clusters; and
place the other hospital in a new cluster of the plurality of clusters when it is determined that the other hospital is not within the threshold distance to the closest one of the plurality of clusters.

19. The CDS system of claim 18, wherein the at least one controller is further configured to create least one CDS tool tailored to each cluster of the plurality of clusters and associate the CDS tool with the corresponding cluster of the plurality of clusters.

20. The CDS system of claim 19, wherein the at least one controller is further configured to render information related to the at least one CDS tool in association with the corresponding cluster of the plurality of clusters.

\* \* \* \* \*